United States Patent
Ittel et al.

(10) Patent No.: US 7,803,881 B2
(45) Date of Patent: Sep. 28, 2010

(54) PROCESS FOR AMINATION OF ACRYLIC MACROMONOMERS AND PRODUCTS THEREFROM

(75) Inventors: Steven Dale Ittel, Wilmington, DE (US); Alexei A. Gridnev, Wilmington, DE (US); Jennifer W. Anderson, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 843 days.

(21) Appl. No.: 11/638,630

(22) Filed: Dec. 12, 2006

(65) Prior Publication Data

US 2007/0260067 A1    Nov. 8, 2007

Related U.S. Application Data

(60) Provisional application No. 60/751,475, filed on Dec. 16, 2005.

(51) Int. Cl.
| | |
|---|---|
| *C08F 20/10* | (2006.01) |
| *C08F 12/28* | (2006.01) |
| *C08F 20/58* | (2006.01) |
| *C08F 22/38* | (2006.01) |
| *C08K 5/34* | (2006.01) |

(52) U.S. Cl. .................. 525/330.3; 524/99; 526/310; 526/304; 526/306

(58) Field of Classification Search ............... 525/330.3, 525/509, 411, 417; 524/99, 428, 612; 526/310, 526/304, 306
See application file for complete search history.

(56) References Cited

U.S. PATENT DOCUMENTS

| | | | |
|---|---|---|---|
| 4,680,352 A | 7/1987 | Janowicz et al. | |
| 4,694,054 A | 9/1987 | Janowicz | |
| 4,886,861 A | 12/1989 | Janowicz | |
| 4,910,268 A * | 3/1990 | Kobayashi | ............ 525/411 |
| 5,028,677 A | 7/1991 | Janowicz | |
| 5,264,530 A | 11/1993 | Darmon et al. | |
| 5,587,431 A | 12/1996 | Gridnev et al. | |
| 5,773,534 A | 6/1998 | Antonelli et al. | |
| 5,883,206 A | 3/1999 | Ittel et al. | |
| 6,117,958 A | 9/2000 | Ittel et al. | |
| 6,624,261 B1 | 9/2003 | Moad et al. | |
| 2007/0142546 A1 | 6/2007 | Ittel et al. | |
| 2009/0012231 A1 | 1/2009 | Ittel et al. | |

OTHER PUBLICATIONS

Ittel et al., "Late-Metal Catalysts for Ethylene Homo-and Copolymerization", Chem. Rev. 2000, 100, pp. 1169-1203.

* cited by examiner

*Primary Examiner*—Ling-Siu Choi
*Assistant Examiner*—Monique Peets

(57) ABSTRACT

Processes for forming adducts of amines with acrylic macromonomers are provided. Also provided are processes for using ring-closing reactions of the adducts to form lactams. The adducts are useful, for example, for making adhesives, surfactants, viscosity modifiers, processing aids, and other products.

14 Claims, 1 Drawing Sheet

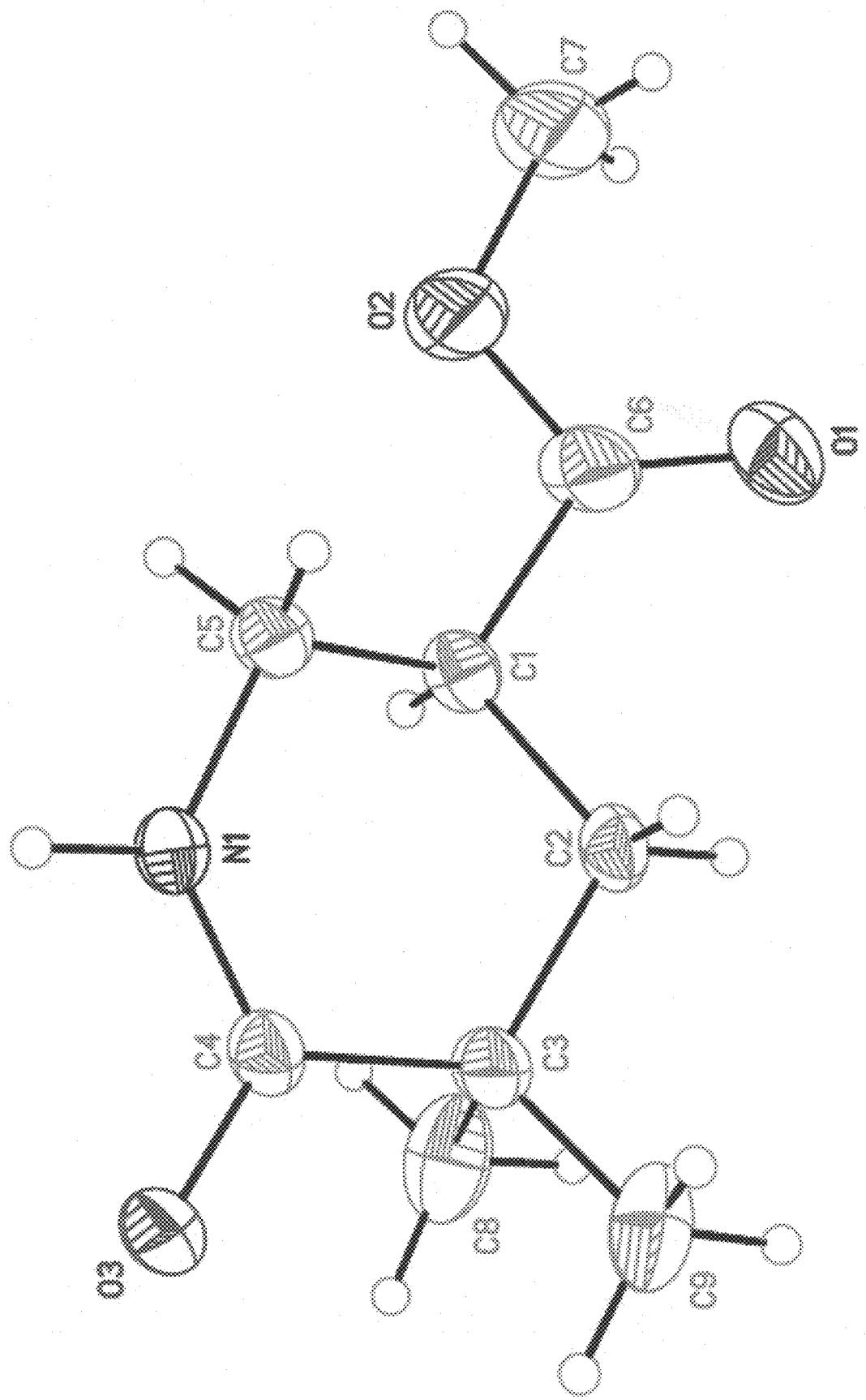

PROCESS FOR AMINATION OF ACRYLIC MACROMONOMERS AND PRODUCTS THEREFROM

CROSS-REFERENCE TO RELATED APPLICATION

This application claims the benefit of U.S. Provisional Application Ser. No. 60/751,475 filed on Dec. 16, 2005 which are hereby incorporated by references in its entirely.

FIELD OF THE INVENTION

The present invention relates to adducts of amines with acrylic oligomers and macromonomers and processes for forming the adducts. The invention further relates to processes for forming lactams using ring-closing reactions of the adducts.

TECHNICAL BACKGROUND

Block copolymers and functionalized macromonomers are essential components of modern dispersants, inks, and paints. They are also utilized in a variety of other applications such as dispersants, crosslinkers, curing agents, stain resists, resists, compatibilizers, and surfactants, to name just a few applications. There is always a need for new block copolymers and functionalized macromonomers with new physical and chemical properties.

Cobalt-catalyzed chain transfer (CCT) in free radical oligomerizations or polymerizations of acrylics is a well-established, commercial technology. The CCT process produces terminally unsaturated macromonomers and the technology is compatible with a wide range of functionalities.

Amine-functionalized compounds are one of the more diverse classes of organic molecules. Thus, a reaction with amines brings a very wide range of new functionalities to their reaction products. Another, more limited but nonetheless significant class of amines is polymeric amines. These range from polymers terminated with a single amine group to polymers in which amine functionality is incorporated into each repeat group in the polymer backbone.

A reaction that combines the range of available CCT macromonomers with the range of available amines would be a powerful tool for the design of new macromonomers and block copolymers for a variety of applications.

SUMMARY OF THE INVENTION

One aspect of the present invention is a compound having the structure

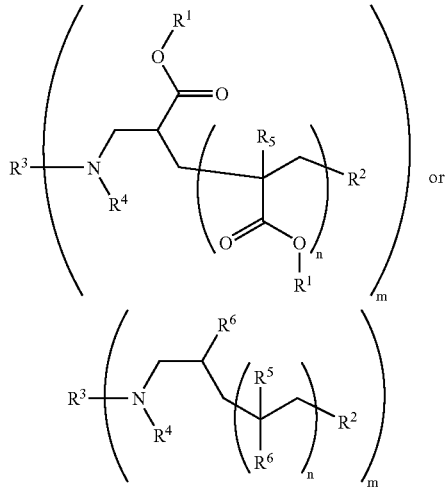

wherein each $R^1$ and $R^2$ are independently H, alkyl of 1-20 carbon atoms, aryl, substituted alkyl of 1-20 carbon atoms, or substituted aryl; $R^3$ and $R^4$ are independently H, alkyl of 1-100 carbon atoms, or substituted alkyl of 1-100 non-hydrogen atoms or $R^3$ is a polymer; $R^5$ is methyl, hydrogen or hydroxymethyl; $n=1-100$; $m=1-100$ and is equal to or less than the number of reactive amino groups on $R^3$, and $R^6$ are independently —CN, —$CO_2R^1$, —$COR^1$, or —$CONR^1R^1$.

Another aspect of the present invention is a compound having the structure

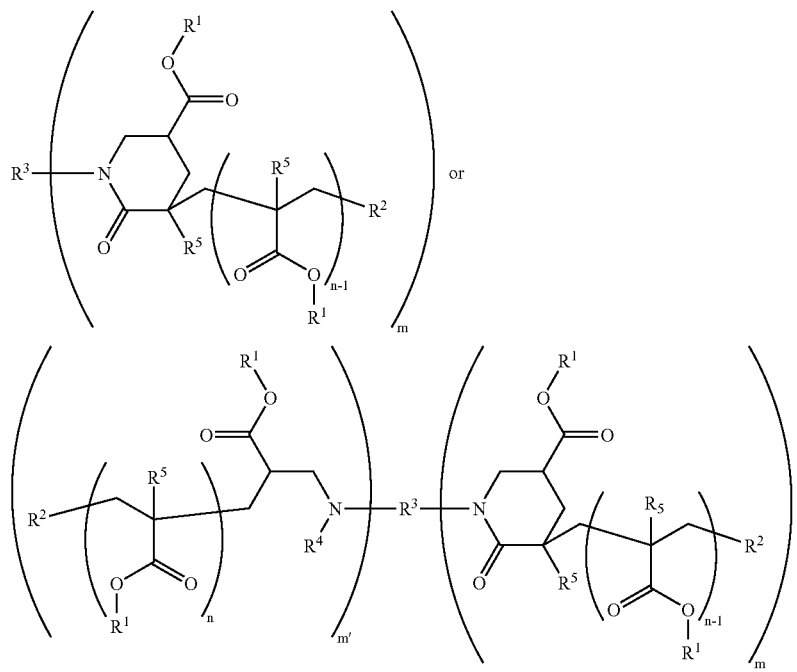

wherein $R^1$ and $R^2$ are independently H, alkyl of 1-20 carbon atoms, aryl, substituted alkyl of 1-20 carbon atoms, or substituted aryl; $R^3$ is H, alkyl of 1-100 carbon atoms, or substituted alkyl or a polymer; $R^5$ is methyl, hydrogen or hydroxymethyl; $n=1$-100; and $m+m'=1$-100 and is equal to or less than the number of reactive amino groups on $R^3$.

A further aspect of the present invention is a process of synthesizing a compound having a formula of:

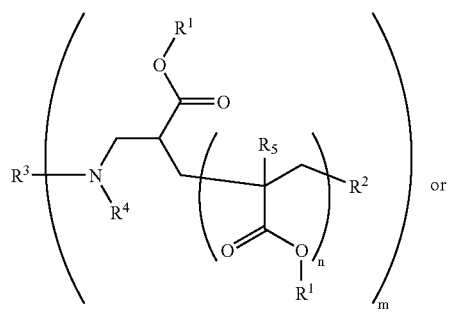

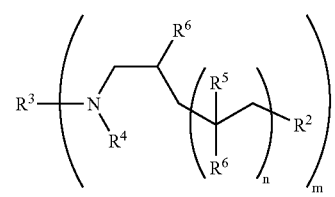

comprising contacting an amine of formula $R^3R^4NH$, with a macromonomer of formula

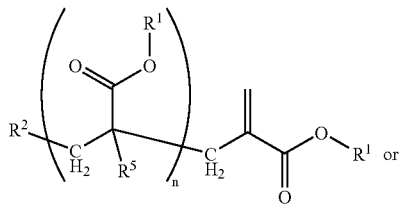

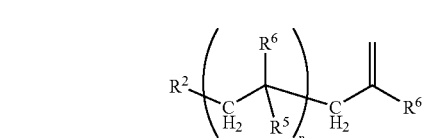

and allowing the amine and the macromonomer to react; wherein $R^1$ and $R^2$ are independently H, alkyl of 1-20 carbon atoms, aryl, substituted alkyl of 1-20 non-hydrogen atoms, or substituted aryl; $R^3$ and $R^4$ are independently H, alkyl of 1-20 carbon atoms, or substituted alkyl of 1-20 non-hydrogen atoms or $R^3$ is a polymer; $R^5$ is methyl, hydrogen or hydroxymethyl; $n=1$-100; $m=1$-100 and is equal to or less than the number of reactive amino groups on $R^3$, and $R^6$ are independently —CN, —$CO_2R^1$, —$COR^1$, or —$CONR^1R^1$.

Another aspect of the present invention is a process of synthesizing a compound of formula:

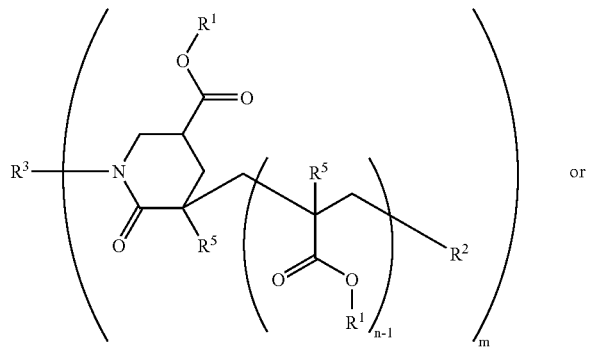

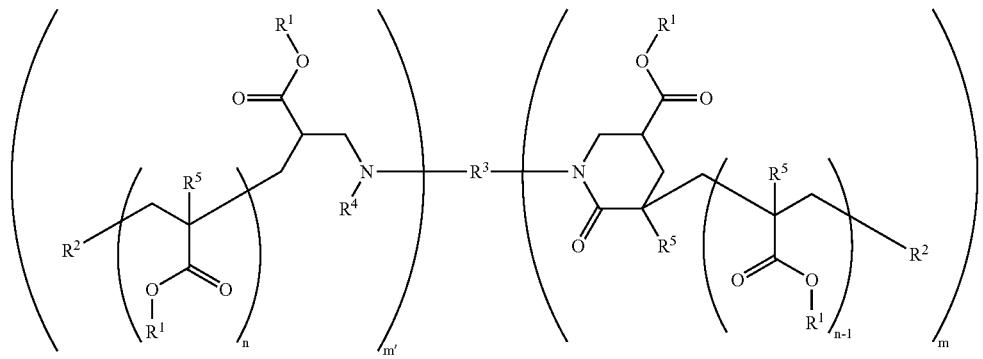

comprising contacting an amine of formula $R^3NH_2$ with a macromonomer of formula

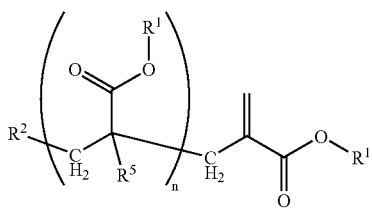

and allowing the amine and the macromoner to react; wherein $R^1$ and $R^2$ are independently H, alkyl of 1-20 carbon atoms, aryl, substituted alkyl of 1-20 nonhydrogen atoms, or substituted aryl; $R^3$ are independently H, alkyl of 1-20 carbon atoms, substituted alkyl of 1-20 non-hydrogen atoms or a polymer; $R^5$ is methyl, hydrogen or hydroxymethyl; n=1-100; m+m'=1-100 and is equal to or less than the number of reactive amino groups on $R^3$ A further aspect of the present invention is a product formed by a process comprising reacting a macromonomer of formula

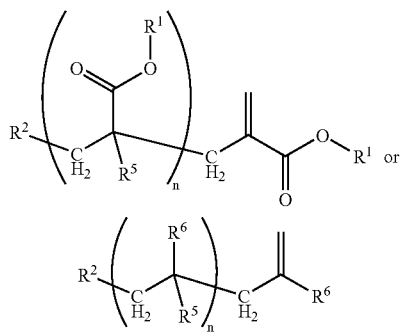

with an amine of formula $R^3R^4NH$; wherein $R^1$ and $R^2$ are independently H, alkyl of 1-20 carbon atoms, aryl, substituted alkyl of 1-20 non-hydrogen atoms, or substituted aryl; $R^3$ and $R^4$ are independently H, alkyl of 1-20 carbon atoms, or substituted alkyl of 1-20 non-hydrogen atoms or $R^3$ is a polymer; $R^5$ is methyl, hydrogen or hydroxymethyl; n=1-100; m=1-100 and is equal to or less than the number of reactive amino groups on $R^3$, and $R^6$ are independently —CN, —$CO_2R^1$, —$COR^1$, or —$CONR^1R^1$.

Another aspect of the present invention is a compound having the structure

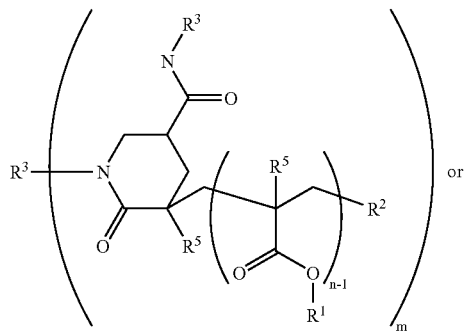

or

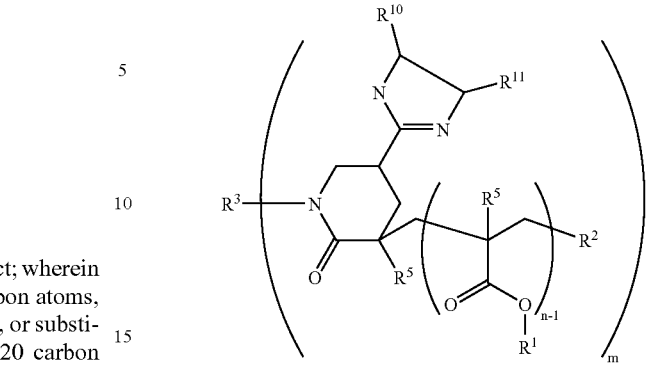

wherein $R^1$ and $R^2$ are independently H, alkyl of 1-20 carbon atoms, aryl, substituted alkyl of 1-20 carbon atoms, or substituted aryl; $R^3$ is H, alkyl of 1-100 carbon atoms, or substituted alkyl or a polymer; $R^5$ is methyl, hydrogen or hydroxymethyl; n=1-100; and m+m'=1-100 and is equal to or less than the number of reactive amino groups on $R^3$; and $R^{10}$ and $R^{11}$ are independently hydrogen or alkyl and may be combined in a cyclic structure.

These and other aspects of the present invention will be apparent to those skilled in the art in view of the present disclosure and the appended claims.

BRIEF DESCRIPTION OF THE FIGURES

FIG. 1 shows an ORTEP drawing of the crystal structure of the cyclized ammonia adduct of the MMA dimer confirming the proposed structure for the most simple cyclized product.

DETAILED DESCRIPTION

One embodiment of the present invention includes compounds having formula (I)

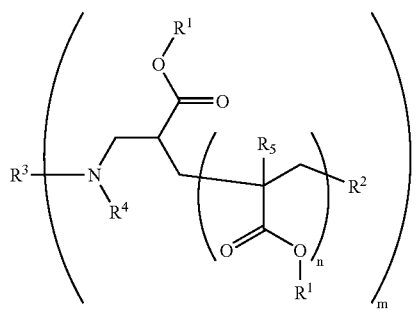

The compounds can be made by the reaction of certain amines with certain macromonomers synthesized by cobalt-catalyzed chain transfer (CCT) in free radical initiated acrylic oligomerizations.

In some embodiments, a process includes subjecting compounds of formula (I) to a ring-closing step, forming compounds having formula

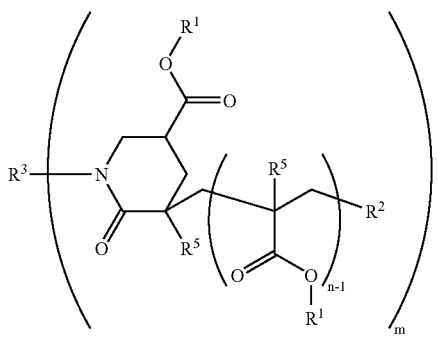

wherein $R^3R^4$—N or $R^3$—N portions of the two molecules are derived from the reacting amine and the remainder of the structure is derived from the CCT macromonomer.

The processes shown using the following structures include reactions with $R^3$-containing molecules having more than one reactive amino group. As an illustrative example of one embodiment, if the reaction is limited to monofunctional primary amines, then the reaction can be represented by the addition

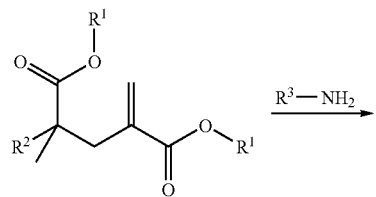

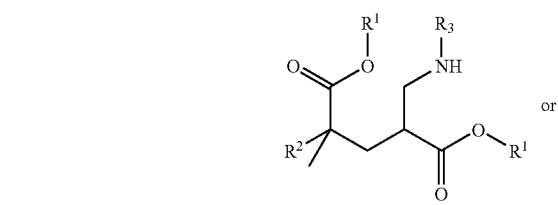

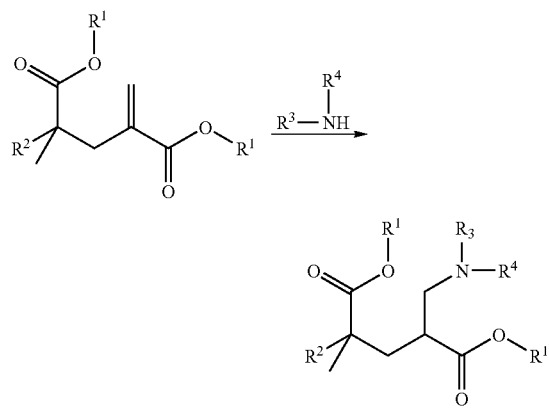

If $R^4$ is a hydrogen atom, then the reaction may proceed further, going through a ring-closing reaction

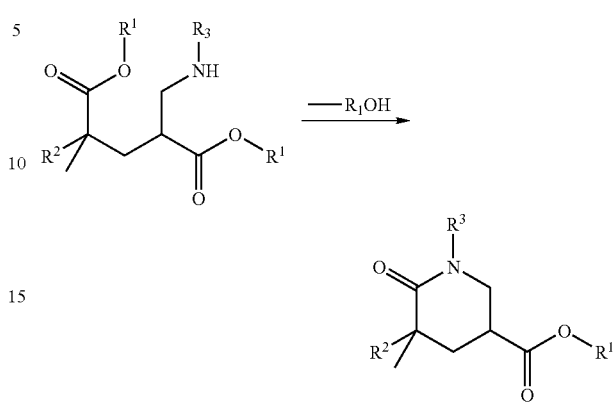

Cobalt-catalyzed chain transfer (CCT) in free radical oligomerizations or polymerizations of acrylics is a well established, commercial technology. The CCT process produces terminally unsaturated macromonomers and the technology is compatible with a wide range of functionalities. Catalytic chain transfer is particularly useful in the polymerization or oligomerization of methacrylates where it yields compounds having the structure wherein each $R^1$ and $R^2$ are independently H, alkyl of 1-20 carbon atoms, aryl, substituted alkyl of 1-20 carbon atoms, or substituted aryl and $R^5$ is methyl, hydrogen or hydroxymethyl, and n=1-100, preferably n=1-50. These and related species are referred to herein interchangeably as "oligomers," or "macromonomers" and the terms are further intended to incorporate the products of copolymerizations of methacrylates with other methacrylates as well as with acrylates and with other free-radically copolymerizable monomers. These oligomers and their production are described in a series of U.S. patents issued to DuPont that include U.S. Pat. No. 6,624,261, U.S. Pat. No. 6,388,036, U.S. Pat. No. 6,117,958, U.S. Pat. No. 5,883,206, U.S. Pat. No. 5,587,431, U.S. Pat. No. 5,028,677, U.S. Pat. No. 4,886,861, U.S. Pat. No. 4,694,054, and U.S. Pat. No. 4,680,352. While there is no intent to limit the molecular weight of the oligomers useful in this invention, they will generally range from dimers (n=1) to species in which n may be hundreds. Most frequently, n will range from 1 to 20.

As used herein, the term "acrylic" is a general term meant to encompass a variety of ethylenically unsaturated monomers and comonomers that may be copolymerized with methacrylate monomers to form the oligomers or macromonomers employed in this disclosure. Thus the resulting macromonomers may comprise a variety of methacrylate ester monomers, acrylate ester monomers, styrene and alpha-methylstyrene, acrylonitrile and methacrylonitrile monomers. Other comonomers such as methylenebutyrolactone, vinylpyrrolidinone, chloroprene, vinyl acetate may also be incorporated into the macromonomers in lesser amounts.

As distinguished from the terms oligomers or macromonomers that are used to describe the acrylic portion of the aminated products described herein, the term "polymer" or "polymeric" is used herein to refer to the portion of the aminated products derived from the amine-containing species and is specified as $R^3$ in the structures above. When $R^3$ is polymeric, the polymer may be derived from monomers such as ethylene oxide, or ethyleneimine. A polymeric system derived from ethylene oxide is terminated with an amino group. A system derived from ethyleneimine contains a plurality of amino groups. Amino-terminated polyethylene or amine-terminated nylon are other examples of polymeric amines suitable for use in this disclosure. $R^3$ also includes species with molecular weights up to a million, or more frequently having molecular weights of hundreds to thousands. The distinction between molecular amines and polymeric amines is based largely upon their derivation and the two classes of species represent a continuum. For example, decylamine may be considered to be a very low molecular weight version of amine-terminated polyethylene, $H(C_2H_4)_nNH_2$ where n=5. Another family of suitable polymeric amine is based upon polymers of 2-aminoethyl methacrylate, so it is possible that $R^3$ incorporates acrylic monomers.

The substituent $R^1$ on the ester group is selected from alkyl or substituted alkyl groups, aryl groups, and substituted aryl groups. The terminal substituent, $R^2$, on the ester group is selected from hydrogen atom, alkyl substituted alkyl aryl and substituted aryl.

By "alkyl" is meant a linear or branched saturated hydrocarbyl unit ranging from methyl, ethyl, propyl, to much higher carbon numbers including polymeric species. Branched alkyl includes isopropyl, isobutyl, sec-butyl, neopentyl, and much higher carbon numbers including polymeric species.

A "substituted alkyl" is an alkyl having a non-hydrogen functionality attached to or in place of any of the carbon atoms of the alkyl. The substituents may be the same or different and selected, for example, from carboxylic ester, hydroxyl, alkoxy, tertiary amino, trifluoromethyl, perfluoroalkyl and other substituted and unsubstituted alkyl, substituted and unsubstituted aryl, substituted and unsubstituted olefin and halogen. Substituted alkyl also includes species in which one or more of the carbon atoms other than the first carbon atom of the alkyl are substituted with heteroatoms such as oxygen, sulfur, silicon, tin or other elements. Substituted alkyl groups generally do not bear functionality that can react with amines under the conditions of the reactions disclosed herein. If such reactions can occur, they are taken into consideration when formulating a stoichiometry for the reaction. For instance, a glycidyl group would be an inappropriate choice of substituted alkyl because it is well known to those skilled in the art that amines will cause a ring-opening reaction of the epoxy functionality. Carboxylic acids will react with the amines to form ammonium salts thereby inhibiting the reaction.

Preferred alkyl or substituted alkyl groups include methyl, ethyl, propyls (all isomers), butyls (all isomers), 2-ethylhexyl, isobornyl, octyl (all isomers), higher normal and branched alkyls, and cyclohexyl. Benzyl and substituted benzyls, neophyl, phenylethyl, and naphthylmethyl are preferred examples of arylalkyls, a class of substituted alkyls. Preferred examples of substituted alkyl groups include 2-hydroxyethyl, 2-hydroxypropyl, trimethylsilylpropyl, methoxyethyl, trimethylsilylmethyl, 11-carbomethoxyundecyl, trimethoxysilylpropyl, methylthiopropyl, trifluoromethyl, 6,6,6-trifluorohexyl, triethoxysilylpropyl, tributoxysilylpropyl, dimethoxymethylsilylpropyl, diethoxymethylsilylpropyl, dibutoxymethylsilylpropyl, diisopropoxymethylsilylpropyl, dimethoxysilylpropyl, diethoxysilylpropyl, dibutoxysilylpropyl, diisopropoxysilylpropyl, 2-(oxyethyl hydrogen propanedioate) and trimethylsilylmethyl.

By "aryl" is meant aromatic groups, including aryl and heteroaryl rings, examples being phenyl, naphthyl, pyridyl, pyrimidyl, benzoxoylanthracenyl.

"Substituted aryl" refers to aromatic groups substituted with functional substituents being the same or different and selected, for example, from carboxylic ester, hydroxyl, alkoxy, amino, secondary amino, tertiary amino, trifluoromethyl, perfluoroalkyl and other substituted and unsubstituted alkyl, substituted and unsubstituted aryl, substituted and unsubstituted olefin and halogen.

The substituent $R^2$ on the oligomer backbone is generally a hydrogen atom, derived from the catalytic chain transfer process, though it is not limited to such. $R^2$ may be selected from alkyls, substituted alkyls, aryls and substituted aryls. $R^2$ may originate from copolymerizations of methacrylic monomers with acrylic monomers, particularly those resulting from cobalt-catalyzed chain transfer as disclosed, for example, in U.S. Pat. No. 6,624,261; from chain initiation with a non-polymerizable monomer as disclosed, for example, in U.S. Pat. No. 6,117,958; or from chain transfer in an acrylic polymerization when methacrylate macromonomers are utilized as chain transfer reagents, as disclosed, for example, in U.S. Pat. No. 5,773,534 and U.S. Pat. No. 5,264,530. Finally, $R^2$ may originate from conventional chemical syntheses or modifications.

Amine-functionalized compounds are one of the most diverse classes of organic molecules. Thus, a reaction with amines can bring a wide range of new functionalities to their reaction products. In preferred embodiments, amine functionalities include amines $R^3$—$NH_2$ and $R^3R^4NH$ wherein the substituents $R^3$ and $R^4$ on the amine are selected from a hydrogen atom, alkyl groups, and functionalized alkyl groups. Preferred functional groups include methyl, ethyl, propyls (all isomers), butyls (all isomers), 2-ethylhexyl, isobornyl, benzyl and substituted benzyls, cyclohexyl, 2-hydroxyethyl, 2-hydroxypropyl, trimethoxysilylpropyl, triethoxysilylpropyl, tributoxysilylpropyl, dimethoxymethylsilylpropyl, diethoxymethylsilylpropyl, dibutoxymethylsilylpropyl, diisopropoxymethylsilylpropyl, dimethoxysilylpropyl, diethoxysilylpropyl, dibutoxysilylpropyl, diisopropoxysilylpropyl, and higher normal and branched alkyls. Further included in the amines are bifunctional amines, polyfunctional amines, and polymeric amines. $R^3$ and $R^4$ may be combined in a cyclic structure. Examples of ring structures include piperidine, piperazine, 4'-piperazineacetophenone. $R^3$ and $R^4$ may be constituents of polyfunctional amines, bifunctional amines or diamines, polyfunctional amines or polymeric amines.

"Bifunctional amine" or "diamine" means an organic moiety having two amino groups that will be active in the reaction or process described herein. Examples would include ethylenediamine, 1,6-hexamethylenediamine, 1,4-bis(aminomethyl)benzene, diamino-terminated polyethyleneoxide, or diaminopropyl-terminated poly(dimethylsiloxane). Hydrazine and substituted hydrazines would be the most simple diamines.

"Polyfunctional amine" means an organic moiety having two or more amino groups that are active in the reactions and processes disclosed herein. Examples include tris(aminoethyl)amine, amino-ethyl-functionalized polystyrene, and aminopropyl-functionalized poly(dimethylsiloxane).

"Polymeric amine" means an amino-containing organic moiety based upon a polymeric backbone. The amino group may be in the backbone of the polymer or may be pendant to it.

The polymeric amines are a more limited but nonetheless significant class of amines. They range from polymers terminated with a single amine group to polymers in which amine functionality is incorporated into each repeat group in the polymer backbone. Examples include diamino-terminated polyethyleneoxide, diaminopropyl-terminated poly(dimethylsiloxane), amino-ethyl-functionalized polystyrene, aminopropyl-functionalized poly(dimethylsiloxane), linear and branched polyethyleneimine and diamine-terminated nylon.

Considering the wide number of classes of amines and the array of acrylic oligomers available, types of products that can be obtained are shown in Table 1. In multiple additions, the products of which are shown in column 3 of Table 1, the macromonomers may be added to the amines sequentially and need not be the same. Thus the oligomer dimer may be an AB copolymer rather than an AA dimer; the ABA block copolymer may be an ABC block copolymer; and the comb AB copolymer may be an A(BB'B") copolymer.

TABLE 1

Possible structural types

|  | Single addition | single cyclization | Multiple addition and or cyclization |
|---|---|---|---|
| Molecular amine | Modified oligomer | Modified oligomer | Not possible |
| Molecular diamine | Modified oligomer | Modified oligomer | Modified AA oligomer dimer |
| Molecular triamine | Modified oligomer | Modified oligomer | Modified AA oligomer dimer or star trimer |
| Polymeric monoamine | AB block copolymer | AB block copolymer | Not possible |
| Polymeric diamine | AB block copolymer | AB block copolymer | ABA block copolymer |
| Polymeric polyamine | AB block copolymer | AB block copolymer | comb AB copolymer |

By "reactive amino groups" is meant those amino groups that are capable of undergoing the reactions described herein, as opposed to "unreactive amino groups." Tertiary amines have no reactive hydrogen atom and are thus incapable of being "reactive amino groups." Other unreactive amino groups are those which are too sterically encumbered to undergo reaction or chemically deactivated by being attached to aromatic groups. A "reactive amino group" may be rendered unreactive by being too close to another reactive amino group in the same molecule such that when the other reactive amino group has reacted, the sterics become too crowded for a second reaction. Tertiary alkyl groups can render amines unreactive as can multiple isoalkyl groups.

As used herein, the term "derived from" refers to the origin of substituents (Q or $R^3$) that are part of the disclosed compositions and that originated from the diverse range of amines that are reacted with the products of catalytic chain transfer. For instance, in a compound derived from the amine $R^3$—$NH_2$ if $R^3$ is octyl, then the substituent octyl is said to have been derived from the amine, octylamine or 1-aminooctane. The products can similarly be derived from diamines $H_2N$-Q-$NH_2$ in which case an oligomer would add to one or preferably both amino groups. For instance, if 1,6-hexanediamine were employed, the Q derived from that reaction would be the hexamethylene group, —$(CH_2)_6$—. When polymeric polyamines are employed, Q becomes the polymeric backbone without the amine groups. It is not expected that addition will be complete; some or many of the pendant amine groups will remain unreacted, particularly if the amine groups are closely spaced down the polymer backbone.

A reaction that combines the range of available CCT macromonomers with the range of available amines is a powerful tool for the design of new macromonomers and block copolymers for a variety of applications. The processes disclosed herein use the reaction of amines with certain oligomers prepared by catalytic chain transfer as described, for example, in Gridnev and Ittel (*Chemical Reviews*, 100(4), 1169, (2000)). The reaction is described by the addition of an amine to 1 to yield the adduct 2.

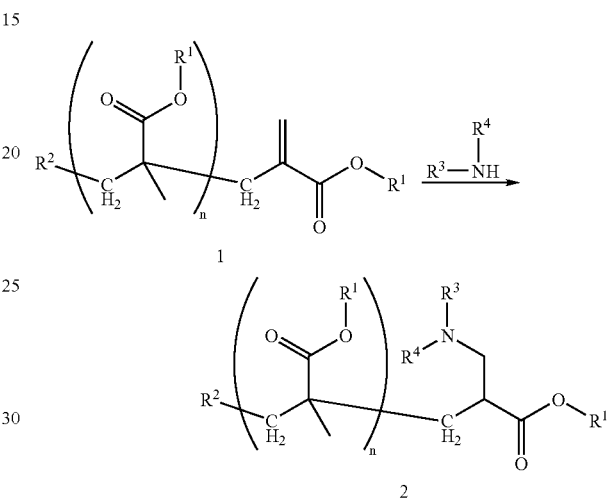

When the substituent $R^4$ on 2 is a hydrogen atom, the disclosure further includes the subsequent reaction of 2 to yield the ring-closed product, 3.

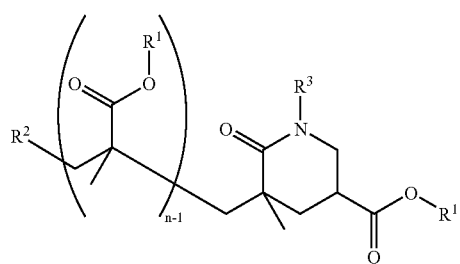

$R^1$, and $R^2$ are independently H, alkyl, aryl, substituted alkyl, or substituted aryl, $R^3$ is H, alkyl, or substituted alkyl, and n=1-100.

The cyclization reaction can be confirmed by the x-ray crystal structure of a product of this reaction—for example, the adduct of ammonia with methyl methacrylate dimer.

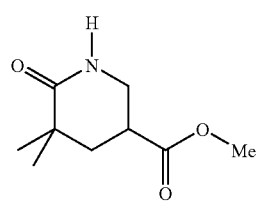

The ORTEP drawing of the structure is shown in FIG. 1. The chair configuration of the six membered ring is confirmed, though there is a disorder in the structure that averages the two possible enantiomers, the chiral center being at the carboxylate group.

In certain reaction sequences, it has been noted that addition of amine to the macromonomer double bond and subsequent cyclization are not the only reactions that take place. Thus in some cases amidation of the ester group is observed to yield amides exemplified by products of the type

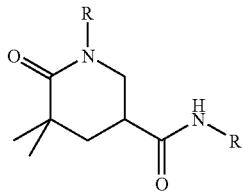

With ethylenediamine, there can be further reaction to give

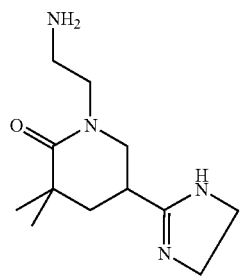

where further dehydration of the amide has led to a terminal imidazoline group. It is known in the macromonomers that the terminal carboxylate groups are more reactive than the internal carboxylate groups. In many of the examples the dimer of MMA has been employed to simplify the analytical characterization of the products, but by definition, in the dimer, the two carboxylate groups are terminal and therefore are expected to be more reactive than in higher oligomers. This will have some effect on the distribution of observed products, the reactions described herein are generalizable.

When the macromonomers are synthesized by the copolymerization of acrylates with methacrylates, it is known that the last monomer incorporated will be a methacrylate and the resulting macromonomer will be terminally, olefinically unsaturated, but there is no control over the penultimate monomer, so it may be methacrylate or acrylate. Thus the amine addition further includes the reaction

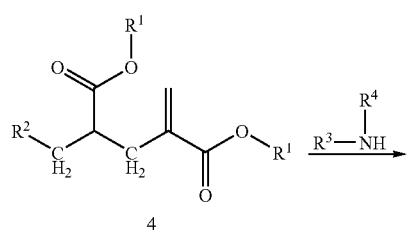

4

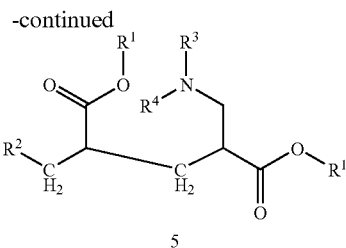

5 where the substituent $R^2$ may be assumed to incorporate the remainder of the random copolymerization product. If $R^4$ is a hydrogen atom, the initial amine addition product, 5, may undergo a further ring closing reaction to yield 6.

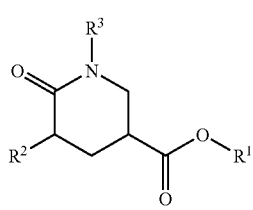

6

If the methacrylate-terminated copolymer has no ester group in the carbon atom β to the olefinic group, then there can be no ring-closing reaction to yield a product such as 6.

The terminal double bond of oligomers of methacrylonitrile can undergo the amination reaction, just as methacrylates, but the cyclization reaction is not available for these products.

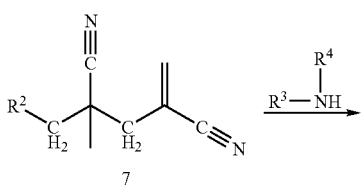

7

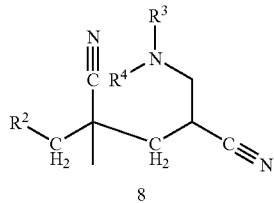

8

Thus, while 7 is reactive, the reaction is complete with the formation of 8.

For the purpose of reaction scouting, it is particularly convenient to employ the dimer of methyl methacrylate as a model for higher molecular weight species. The products would be 2 and 3 wherein n=1, $R^1$=methyl and $R^2$ is a hydrogen atom. The molecular mass of the dimer is a convenient 200. Thus reactions are easily followed by gas chromatography (GC) particularly when it is linked with mass spectroscopy (GC/MS). The initial product would have a mass of 200 plus the mass of the amine and the ring-closing product would be 200 plus the mass of the amine less the mass of methanol.

The kinetics of the reactions may be followed conveniently by taking samples for analysis as a function of time. Sequential NMR spectra are another convenient method for following the course of the reaction.

The reactions may be carried out in a solvent for convenience, but in general they are desirably carried out with neat reagents. The reactions will take place at room temperature, but it is generally more convenient to carry them out more rapidly at elevated temperatures. As indicated above, the addition can be carried out in the absence of, or in the presence of, any medium or "solvent" that does not otherwise interfere with the reaction. These include alcohols such as isopropanol; amides such as dimethyl formamide; aromatic hydrocarbons such as toluene and xylene; ethers such as tetrahydrofuran and dibutyl ether; ethylene glycol; glycol ethers, alkyl esters or mixed ester ethers such as monoalkyl ether-monoalkanoates. Mixtures of two or more solvents can be used. Amines containing unreactive amino groups may also be employed as solvents, but in general, amines are not preferred. In general the solvent should have a boiling point higher than the desired reaction temperature so that the reaction may be carried out at elevated temperatures without the need for employing pressure-containing equipment. As used herein, the term "solvent" also refers to media utilized in the preparation of automotive finishes and other paints from the adducts formed according to the processes disclosed herein.

The amine adduct and the ring-closed products are useful in a wide variety of coating and molding applications. Other uses include cast, blown, spun or sprayed applications in fiber, film, sheet, composite materials, inks, paints, and multilayer coatings. They may be utilized in those end-uses as adhesives, adhesion promoters, biological agents, compatibilizers, coupling agents, crosslinkers, curing agents, dispersants, de-foamers, emulsifiers, flocculent, grafting agents, photopolymerizable materials, resists, stabilizers, surface active agents, surfactants, viscosity modifiers, and for other desirable properties. End products taking advantage of available characteristics can include, for example, automotive and architectural coatings or finishes, including high solids, aqueous, or solvent-based finishes.

EXAMPLES

Some polymers were from Scientific Polymer Products located in Ontario, N.Y. Most other materials were from Aldrich Chemical located in St. Louis, Mo. The oligomers of methyl methacrylate were prepared by DuPont at its Marshall Laboratory facility using literature methods. MMA dimer was prepared by running a CCT reaction of methyl methacrylate with a high catalyst loading to synthesize mostly dimer low oligomers and then the purified dimer was distilled from the reaction mixture.

Gas chromatography was carried out on an HP-5890 gas chromatograph (Agilent Technologies, Santa Clara, Calif.) equipped with a flame ionization detector (FID) and autosampler and using a Phenomenex (Phenomenex Inc., Torrance, Calif.) ZB-5 column, 30 m×0.32 mm ID×0.25 micron with a one microliter injection. The GC method was programmed to start at 70° C. for 4 min, followed by temperature ramping to 300° C. at a rate of 10° C./min; the final temperature was held for 17 min. The masses of the various components were determined with an HP-6890 gas chromatograph equipped with an HP-5973 mass selective detector (MSD) and autosampler and using a J&W Scientific DB-5MS column (Agilent Technologies, Santa Clara, Calif.), 30 m×0.25 mm ID×0.25 micron column with a one microliter injection. The GC method was programmed to start at 70° C. for 4 min, followed by temperature ramping to 300° C. at rate of 10° C./min; the final temperature was held for 7 min.

Matrix-Assisted Laser Desorption/Ionization (MALDI) mass spectra were obtained on an Applied Biosystems Voyager DE-STR MALDI mass spectrometer (Applied Biosystems, Foster City, Calif.). Samples were prepared by co-crystallizing the analyte solution with a UV-absorbing matrix (2,5-dihydroxybenzoic acid) onto a stainless steel target plate which was introduced to the mass spectrometer under high vacuum (about 2e-7 torr). Irradiation with a nitrogen laser at 337 nm was used to transfer the analyte to the gas phase, where $Na^+$ or $K^+$ cations ionized the molecules. A voltage of 20 kV was applied to accelerate the ions to determine their mass by time of flight.

The size exclusion chromatography method used to measure the molecular weight distribution in these systems utilized an Alliance 2690 from Waters Corporation (Milford, Mass.), with a Waters 410 refractive index detector (DRI). The software for data reduction was Trisec® Conventional GPC version 3.0 by Viscotek (Viscotek, Houston, Tex.). The columns were two PL Gel Mixed C and one PL Gel 500A columns from Polymer Laboratories (Varian, Inc., Palo Alto, Calif.). The mobile phase was unstabilized THF. Chromatographic conditions were 35° C. at a flow rate of 1.00 ml/min, an injection volume of 100 μl and a run time of 50 min. Samples were dissolved for 4 hours in the mobile phase solvent at RT with moderate agitation. Standards for column n calibration were a set of 10 narrow polydispersity (<1.1) poly(methyl methacrylate) (PMMA) standards with peak molecular weights from 1680 through 1,399,000 available from Polymer Laboratories. The column calibration method with PMMA narrow standards utilized a third order of polynomial fit.

Example 1

Reaction of Hexyl Amine with MMA Oligomers

This Example demonstrates the amination of an oligomer mixture and a linear amine.

To a 20 mL vial equipped with stir bar was added methyl methacrylate oligomers (5.00 g, DuPont Marshall Laboratories, Philadelphia, Pa.) and hexylamine (2.53 g, Aldrich, Milwaukee, Wis.). This was allowed to stir at ambient temperature and monitored by gas chromatography. While this reaction was carried out with a mixture of oligomers, the gas chromatographic technique was limited to observing the dimer and trimer reactions. The dimer (Mass=200) and trimer (Mass=300) started to disappear as two new products, the simple hexylamine adducts

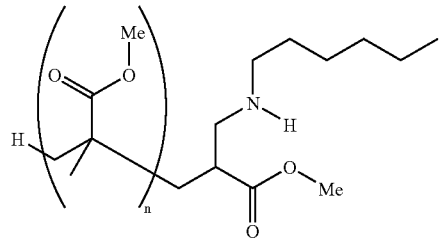

where n=1 (Mass=301) and 2 (Mass 401) started to grow in. These adducts were confirmed by their mass spectra peaks. It was noted that shortly thereafter, two additional products started to grow in. Those were identified as

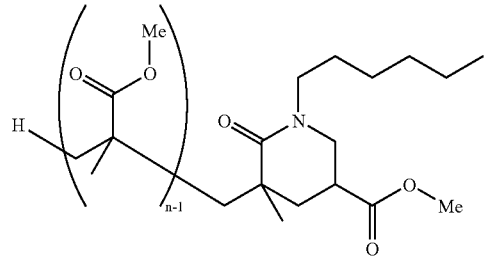

where n=1 (Mass=269) and 2 (Mass=369). These two products continued to grow in with time at the expense of the initial adducts that reached a peak concentration and then started to diminish. The peak for the trimer cyclized adduct was obscured and is not included in the graph. The curves on the plot are typical of a sequential reaction

A+B→C→D where A and B react to form a initial product that then reacts further to give a final product.

Example 2

Reaction of Ammonia with MMA Dimer

A 2 M methanolic solution of ammonia (6.2 mL, Aldrich, Milwaukee, Wis.) was reacted with MMA dimer (2.50 g, DuPont Marshall Laboratories, Philadelphia, Pa.) under the conditions of Example 1, but the reaction was heated to 60° C. Some ammonia was lost during the reaction, so it was replenished several times. NMR and mass spectrometry were consistent with the proposed ring-closed structure.

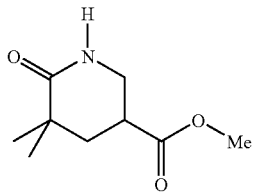

The material in the vial would crystallize when allowed to come to room temperature. Crystals were submitted for X-ray analysis. The ORTEP drawing of the crystal structure of the adduct is shown in FIG. 1, confirming the proposed structure. There was a disorder in the crystal structure superimposing the two enantiomers of the compound upon one another.

The NMR spectrum of the material is as follows: Me, 1.18 (3H, sing), 1.22 (3H, sing); $NCH_2$, 1.85 (1H, trip), 1.97 (1H, mult); $CO_2MeCH$, 2.95 (1H, Trip of doub of doub); $Me_2CCH_2$ 3.35 (1H, trip), 3.44 (1H, mult); $OCH3$ 3.70 (3H, s); NH, 6.24 (1H, broad).

Example 3

Reaction of Benzylamine with MMA Dimer

This Example demonstrates amination with an aralkyl amine.

Benzylamine (2.68 g, Aldrich, Milwaukee, Wis.) was reacted with MMA dimer (5.00 g, DuPont Marshall Laboratories, Philadelphia, Pa.) in the manner of Example 1, but the reaction was heated to 60° C. Characterization of the reaction mixture by gas chromatography after one hour showed the clear presence of

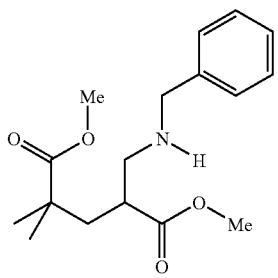

at a mass of 307. After a second hour at 60° C. the peak for the ring-closed product at mass 275

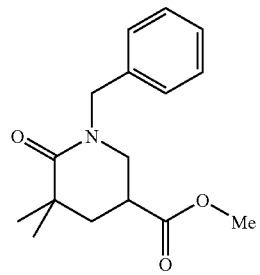

was clearly present. At six hours, the temperature was increased to 80° C. and by 7 hours, the dominant peak was that of the ring-closed product. At prolonged heating times it was observed that the other methyl ester group exchanged with further benzylamine to give the amide product

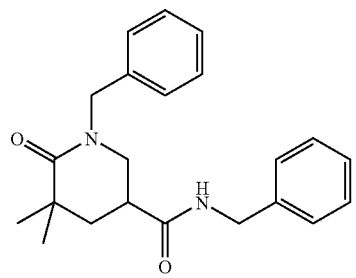

Example 4

Reaction of Cyclohexylamine with MMA Dimer

This Example demonstrates amination using a secondary alkyl amine.

Cyclohexylamine (2.48 g, Aldrich, Milwaukee, Wis.) was reacted with MMA dimer (5.00 g, DuPont Marshall Laboratories, Philadelphia, Pa.) in the manner of Example 1, but the reaction was heated to 60° C. Characterization of the reaction mixture by gas chromatography after one hour showed the clear presence of

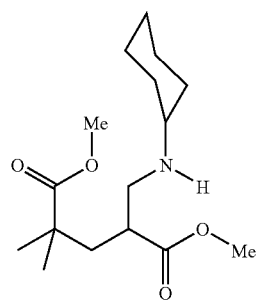

and after 6 hours, conversion was 50%. There was no observable ring-closure product at this point, and the temperature was increased to 90° C. After 28 hours, the ring-closure product

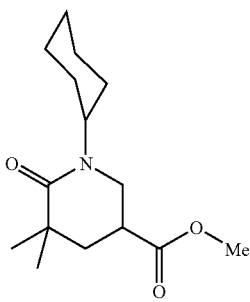

was clearly evident and after 100 hours, the total conversion was over 90% with the ring-closure product being over 50% of the product of the reaction.

Example 5

Reaction of Ethanolamine with MMA Dimer

This Example demonstrates amination with a functional amine.

Ethanolamine (1.53 g, Aldrich, Milwaukee, Wis.) was reacted with MMA dimer (5.00 g, DuPont Marshall Laboratories, Philadelphia, Pa.) in the manner of Example 1, but the reaction was heated to 65° C. after reacting 11 days at room temperature. Characterization of the reaction mixture by gas chromatography after twenty hours showed the clear presence of the ring-closure product

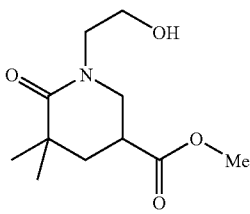

was clearly evident and after 11 days, the total conversion was over 80% with the ring-closure product being over 80% of the product of the reaction. Some ethanolamine was lost during the heating, so an additional amount (1 g) was added. The simple adduct

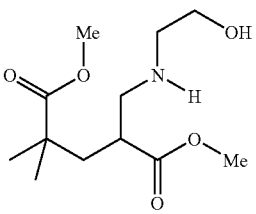

at mass 261, was not observed. At longer reaction times or higher temperatures, additional unidentified, higher-mass products, and these products could become appreciable.

Example 6

Reaction of Dibutyl Amine with MMA Dimer

This example demonstrates amination with a secondary amine.

Dibutylamine (1.62 g, Aldrich, Milwaukee, Wis.) was reacted with MMA dimer (2.50 g, DuPont Marshall Laboratories, Philadelphia, Pa.) in the manner of Example 1, but the reaction at room temperature. Characterization of the reaction mixture by gas chromatography after up to seven days showed none of the desired

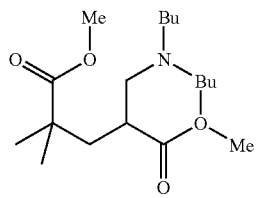

However, after heating to 65° C. for 24 hours, the product was clearly evident and after 8 days at that temperature, conversion to the desired product was several percent.

Example 7

Reaction of Piperidine with MMA Dimer

This Example demonstrates amination with a cyclic secondary amine.

Piperidine (2.13 g, Aldrich, Milwaukee, Wis.) was reacted with MMA dimer (5.00 g, DuPont Marshall Laboratories, Philadelphia, Pa.) in the manner of Example 1, at room temperature. Characterization of the reaction mixture by gas chromatography after eighteen hours showed the clear presence of the simple adduct

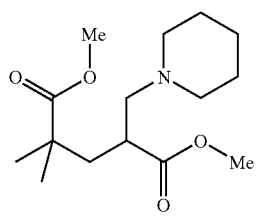

with a mass of 285. After 3 days, conversion to the desired product was over 80%. Heating to 65° C. for an additional 48 hours took the conversion to 96%.

NMR spectrum: A,B, 1.09 (3H, s), 1.12 (3H, s); C, 1.38 (2H, br quintet); D 1.48, (4H, br mult); E 1.66 (1H, dd, J=12, 2 Hz); F 1.88 (1H, dd, J=12, 8); G 2.18 (1H, dd, J=10, 5); H 2.25 (2H, br mult); I 2.48 ((2H, br mult); J 2.41 (1H, dd, J=10, 7) K 2.60 (1H, dddd, J=8, 7, 5, 2); L,M 3.58 (3H, s) 3.59 (3H, S) for the structural assignments given by:

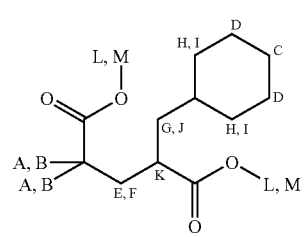

Several broad resonances were observed in the NMR spectrum, indicating that the six-membered ring was undergoing ring inversion at a rate close to but slower than the NMR time-scale.

Example 8

Reaction of Octylamine with MMA Oligomer and Mass Spectrometry of Reaction Product Example was rerun using octylamine (12.93 g, Aldrich, Milwaukee, Wis.) and the sample was analyzed by MALDI. The peaks observed correspond to the mass of the MMA oligomers (20.00 g, DuPont Marshall Laboratories, Philadelphia, Pa.) plus one octylamine (129) plus the H$^+$ ion. The relative intensities of the various products are given in Table 2 and are reflective of the relative abundance of the starting MMA oligomer and octylamine.

TABLE 2

Observed masses and intensities of octylamine adducts with MMA oligomers

| Mass | Relative abundance |
|---|---|
| 330 | 100 |
| 430 | 98 |
| 530 | 90 |
| 630 | 62 |
| 730 | 32 |
| 830 | 15 |
| 930 | 8 |
| 1030 | 5 |
| 1130 | 3 |
| 1230 | 2 |
| 1330 | 1 |

Example 9

Reaction of Jeffamine® XTJ-505® with MMA Dimer

This Example demonstrates amination with a polymeric amine Jeffamine® XTJ-505® (Huntsman Chemical, Houston, Tex.), an amine-terminated copolymer of propylene oxide (PO) and ethylene oxide (EO), is reported to have the approximate average structure

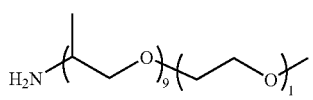

A MALDI mass spectrum indicated that the most abundant peak is that at 540 m consisting of 8 POs and one EO. There is no evidence of oligomers having no or two EOs.

The mixed oligomers (5.00 g, Huntsman Chemical, Houston, Tex.) were reacted with the dimer of methyl methacrylate (MMAD) (1.65 g, DuPont Marshall Laboratories, Philadelphia, Pa.) at 60° C. for 24 hours. The MALDI mass spectrum was run and the results are given in Table 3.

TABLE 3

Mass spectra of Jeffamine 505 and its adduct with MMA dimer.

| Number of PO | Mass of PO + Ends | Mass + 1 EO | Relative Intensity | MASS + 1 PO + MMAD | Relative Intensity |
|---|---|---|---|---|---|
| 0 | 32 | 76 | | 276 | |
| 1 | 90 | 134 | | 334 | |
| 2 | 148 | 192 | | 392 | |
| 3 | 206 | 250 | 5 | 450 | |
| 4 | 264 | 308 | 22 | 508 | 10 |
| 5 | 322 | 366 | 46 | 566 | 18 |
| 6 | 380 | 424 | 78 | 624 | 32 |
| 7 | 438 | 482 | 94 | 682 | 42 |
| 8 | 496 | 540 | 100 | 740 | 46 |
| 9 | 554 | 598 | 96 | 798 | 42 |
| 10 | 612 | 656 | 86 | 856 | 35 |
| 11 | 670 | 714 | 72 | 914 | 25 |
| 12 | 728 | 772 | 48 | 972 | 18 |
| 13 | 786 | 830 | 30 | 1030 | |
| 14 | 844 | 888 | 18 | 1088 | |
| 15 | 902 | 946 | 10 | 1146 | |

The envelope of peaks of the initial adduct was cleanly shifted to a mass 200 units higher than the unreacted material. The conversion was approximately 30% for every mass, and the only appreciable product observed was

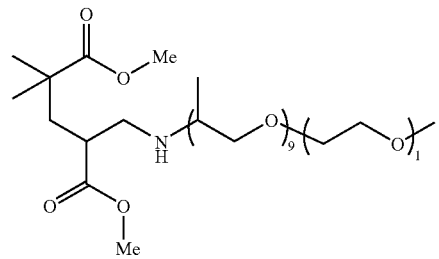

There were trace peaks that could be attributed to the ring-closed product

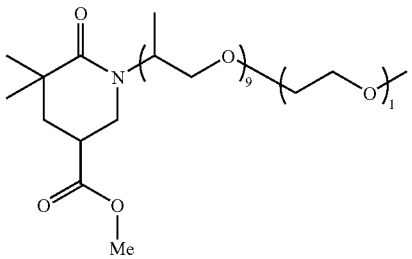

but it would not be expected that this secondary conversion would be appreciable under the conditions employed.

Example 10

Reaction of Jeffamine® XTJ-506® with MMA Dimer

This example demonstrates amination with a polymeric monoamine.

Jeffamine XTJ-506® (Huntsman Chemical, Houston, Tex.) is reported to have the approximate average structure

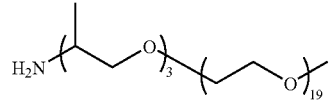

A MALDI mass spectrum indicated that the most abundant peak is that at 540 m consisting of 2 POs and 17 EO. There is no evidence of oligomers having no POs but products having one, two, three and four are abundant, leading to a very complex mass spectrum. The product (5.00 g, Huntsman Chemical, Houston, Tex.) was reacted with methyl methacrylate dimer (0.97 g, DuPont Marshall Laboratories, Philadelphia, Pa.) for 24 hours at 60° C. and then the mixture was submitted for a MALDI mass spectrum the data for which is summarized in Table 4. The top half of the table details the spectrum of the unreacted oligomer and the various observed masses and their intensities. In addition to the starting material, the other product observed is

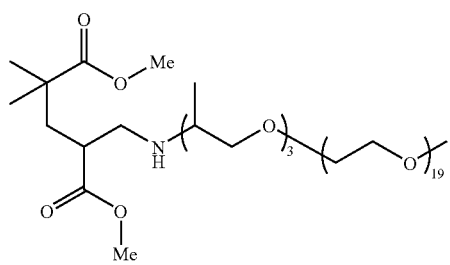

with the observed masses and their intensities being presented in the bottom half of the table. It is clear that the envelope of peaks for the product mirrors the envelope of the peaks for the starting material but with the additional mass of 200 units resulting from the addition of the MMA dimer. Further reaction to the cyclized product

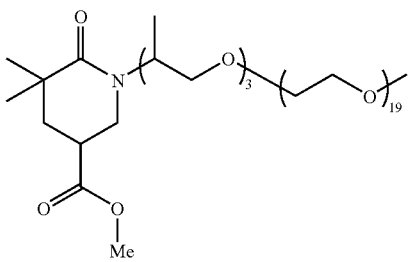

was not observed in these particular spectra.

TABLE 4

Mass spectra of Jeffamine 506 ® and its adduct with MMA dimer.

Masses of Starting Jeffamine ® mixture

| Number of EO | Mass of EO + Ends | Mass + 1 PO | Relative Intensity | Mass + 2 PO | Relative Intensity | Mass + 3 PO | Relative Intensity | Mass + 4 PO | Relative Intensity |
|---|---|---|---|---|---|---|---|---|---|
| 8 | 384 | 442 | | 500 | | 558 | | 616 | |
| 9 | 428 | 486 | | 544 | | 602 | | 660 | |
| 10 | 472 | 530 | | 588 | | 646 | | 704 | |
| 11 | 516 | 574 | | 632 | 28 | 690 | 25 | 748 | |
| 12 | 560 | 618 | | 676 | 40 | 734 | 34 | 792 | |
| 13 | 604 | 662 | 22 | 720 | 55 | 778 | 45 | 836 | |
| 14 | 648 | 706 | 28 | 764 | 66 | 822 | 55 | 880 | |
| 15 | 692 | 750 | 36 | 808 | 85 | 866 | 62 | 924 | |
| 16 | 736 | 794 | 44 | 852 | 94 | 910 | 76 | 968 | 30 |
| 17 | 780 | 838 | 46 | 896 | 100 | 954 | 85 | 1012 | 36 |
| 18 | 824 | 882 | 36 | 940 | 90 | 998 | 70 | 1056 | 34 |
| 19 | 868 | 926 | 28 | 984 | 70 | 1042 | 60 | 1100 | 30 |
| 20 | 912 | 970 | 24 | 1028 | 56 | 1086 | 52 | 1144 | 24 |
| 21 | 956 | 1014 | 22 | 1072 | 48 | 1130 | 38 | 1188 | 20 |
| 22 | 1000 | 1058 | 20 | 1116 | 35 | 1174 | 32 | 1232 | 18 |
| 23 | 1044 | 1102 | 18 | 1160 | 30 | 1218 | 28 | 1276 | 16 |
| 24 | 1088 | 1146 | 16 | 1204 | 26 | 1262 | 24 | 1320 | 12 |
| 25 | 1132 | 1190 | | 1248 | 22 | 1306 | 18 | 1364 | |

Masses of MMA dimer adducts to Jeffamines

| Number of EO | Mass + 1 PO + MMAD | Relative Intensity | Mass + 2 PO + MMAD | Relative Intensity | Mass + 3 PO + MMAD | Relative Intensity | Mass + 4 PO + MMAD | Relative Intensity |
|---|---|---|---|---|---|---|---|---|
| 8 | 642 | | 700 | | 758 | | 816 | |
| 9 | 686 | | 744 | | 802 | | 860 | |
| 10 | 730 | | 788 | | 846 | | 904 | |
| 11 | 774 | | 832 | 4 | 890 | | 948 | |
| 12 | 818 | | 876 | 6 | 934 | | 992 | |
| 13 | 862 | | 920 | 8 | 978 | 5 | 1036 | |
| 14 | 906 | 3 | 964 | 9 | 1022 | 6 | 1080 | |
| 15 | 950 | 3 | 1008 | 11 | 1066 | 10 | 1124 | |
| 16 | 994 | 3 | 1052 | 12 | 1110 | 8 | 1168 | 4 |
| 17 | 1038 | 3 | 1096 | 12 | 1154 | 10 | 1212 | 5 |
| 18 | 1082 | 3 | 1140 | 11 | 1198 | 10 | 1256 | 5 |
| 19 | 1126 | 3 | 1184 | 10 | 1242 | 7 | 1300 | 5 |
| 20 | 1170 | 4 | 1228 | 8 | 1286 | 7 | 1344 | 4 |
| 21 | 1214 | 4 | 1272 | 8 | 1330 | 6 | 1388 | 4 |

TABLE 4-continued

| \multicolumn{8}{c}{Mass spectra of Jeffamine 506 ® and its adduct with MMA dimer.} |
|---|---|---|---|---|---|---|---|
| 22 | 1258 | 3 | 1316 | 6 | 1374 | 5 | 1432 |
| 23 | 1302 | 2 | 1360 | 5 | 1418 | | 1476 |
| 24 | 1346 | 2 | 1404 | | 1462 | | 1520 |
| 25 | 1390 | 2 | 1448 | | 1506 | | 1564 |

Example 11

Reaction of (aminopropyl)trimethylsilane with MMA Dimer

This Example demonstrates amination with a silylated amine.

Methyl methacrylate dimer (2.00 g, DuPont Marshall Laboratories, Philadelphia, Pa.) was weighed into a 20 mL vial. (3-Aminopropyl)trimethylsilane (1.31 g, Gelest SIA0612.0) was added and the mixture was shaken giving a colorless, homogeneous liquid. The sample was analyzed by gas chromatography and mass spectroscopy as a function of time. The first product to grow into the spectrum and observed by GC/MS had a mass of 332, for the expected product as the protonated ion.

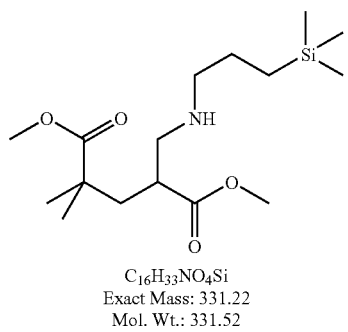

$C_{16}H_{33}NO_4Si$
Exact Mass: 331.22
Mol. Wt.: 331.52

That product was followed in time by a second product having a mass of 300 as expected for the cyclized product in its protonated form.

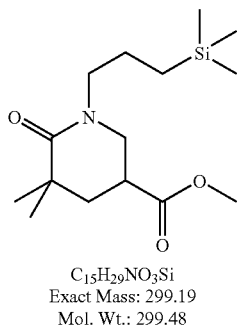

$C_{15}H_{29}NO_3Si$
Exact Mass: 299.19
Mol. Wt.: 299.48

Both of these products, but particularly the initial adduct were unusual in that the parent ion (plus proton) was relatively weak in the mass spectrum.

Example 12

Variation of Amine Concentration

Methyl methacrylate oligomer (20 mL, DuPont Marshall Laboratories, Philadelphia, Pa.) was reacted with the indicated quantity of butylamine (Aldrich, Milwaukee, Wis.), by mixing in a vial that was then tightly sealed and held for two days at room temperature. Small portions of the resulting materials were analyzed by low MW GPC. Samples for NMR spectroscopy were first stripped of low molecular weight materials on a Rotovap (Büchi) under high vacuum at 50° C. and then dissolved in acetone-$d_6$. For 7.9 mL of butylamine (0.08 mol), the unreacted methacrylate was 30%. For 9.9 mL of butylamine (0.10 mol), the unreacted methacrylate was 14%. For 12 mL of butylamine (0.12 mol), the unreacted methacrylate was 4%. This clearly demonstrates that for fixed set of conditions, conversion of the MMA oligomer is higher with increasing amine concentration.

Example 13

Reaction with Ethylenediamine

It was thought that the simplest possible example of a reaction of a diamine with an oligomer would be the reaction of MMA dimer with ethylene diamine. The expected products would be the simple bis-adduct

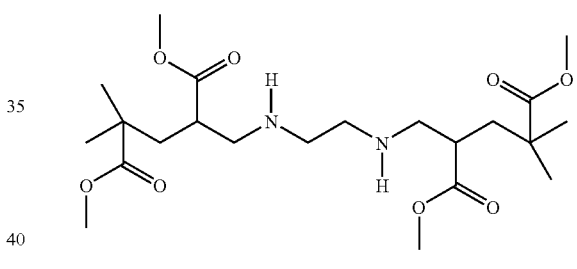

the ring cyclized adduct

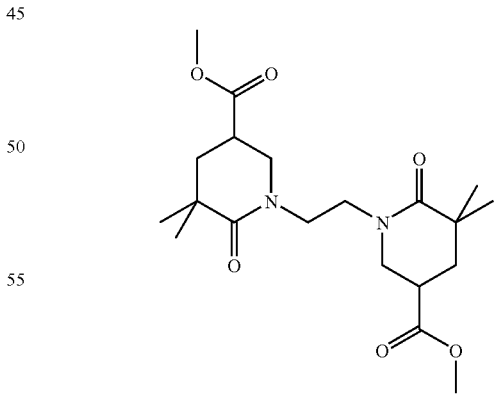

and the cross product with one simple adduct and one cyclization. The course of the reaction was followed by NMR spectroscopy, GC/MS and MALDI-MS as a function of time at various stoichiometries.

Immediately upon mixing at room temperature, there was a color change to yellow indicating the formation of an initial adduct. NMR spectroscopy indicated that the olefinic double bond was completely consumed within an hour at room temperature. Mass spectroscopy indicates similar kinetics and that the initial simple adduct quickly grows in.

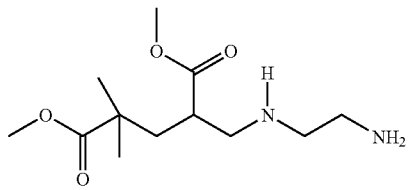

The single NMR signal from the two equivalent methyl groups splits into two peaks as the expected addition introduced asymmetry into the molecule as expected for the simple adduct.

Mass spectroscopy indicated that the initial simple adduct was then consumed to give a second product. Methanol was liberated in the same timeframe indicating that the secondary product was the cyclization product. The methanol proton (4.1 ppm) is exchangeable with the ethylenediamine (1.3 ppm) on the NMR timescale so the cumulative resonance migrated across the spectrum from the initial 1.3 ppm to about 2.7 ppm as more methanol was liberated. The first and second products have very similar retention times and were initial adduct and its cyclization product.

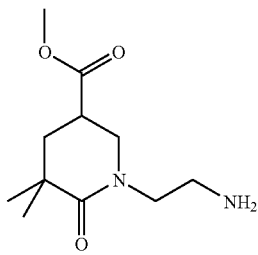

GC/MS showed that the second adduct was further consumed as it went to a third product and possibly a fourth product. The third and fourth products were at longer retention times and were attributed to the addition of a second dimer to the ethylene diamine and the cyclization products.

With excess ethylene diamine, there were additional products. The first thing that was observed was that an insoluble product was formed and that the product was not visible by gas chromatography. It was also observed that a resonance at 8.5 ppm began to grow into the NMR spectra. The insoluble material was analyzed by MALDI mass spectroscopy. Their peaks could be attributed to the compositions of matter

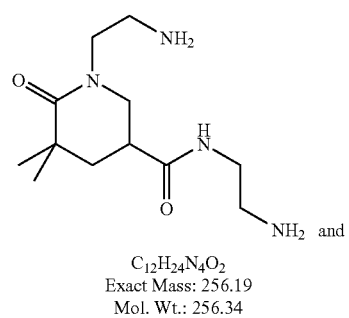

$C_{12}H_{24}N_4O_2$
Exact Mass: 256.19
Mol. Wt.: 256.34

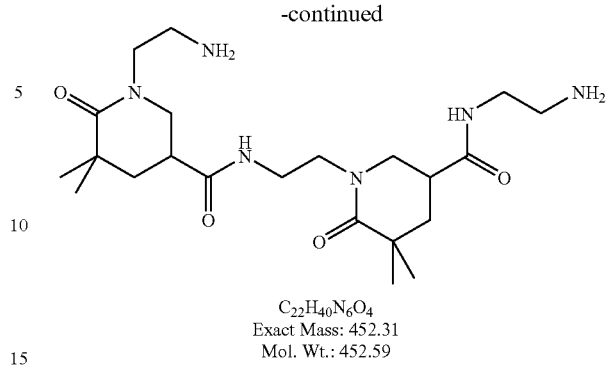

$C_{22}H_{40}N_6O_4$
Exact Mass: 452.31
Mol. Wt.: 452.59 and the next two higher oligomers. In addition to this series of oligomers, peaks for the compositions of matter

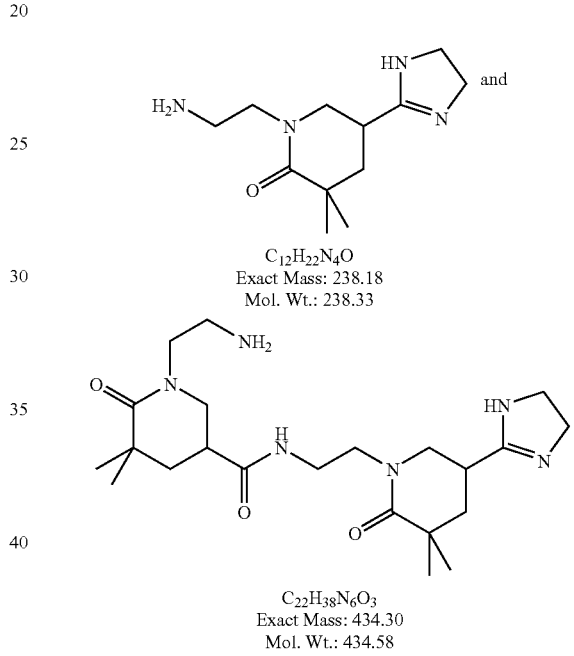

$C_{12}H_{22}N_4O$
Exact Mass: 238.18
Mol. Wt.: 238.33

$C_{22}H_{38}N_6O_3$
Exact Mass: 434.30
Mol. Wt.: 434.58 were observed. The NMR resonances at 8.5 ppm were attributed to the terminal imidazoline group.

Example 14

Reaction with Polyethyleneimine

This Example shows the use of a polymeric polyamine.
Polyethyleneimines (PEI) have a structure approximated by the equation

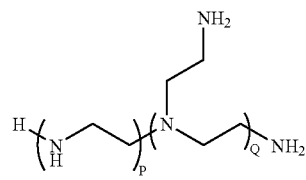

In polymers where P is large relative to Q, the polymer is referred to as linear, and it is referred to as branched when Q is large relative to P. Polyethyleneimine (Aldrich, Milwaukee, Wis., catalog number 4685533) is described as a mixture of linear and branched polyethyleneimines with P+Q of about 10. It was found to contain cyclic oligomers also.

Polyethyleneimine (4.23 g, Aldrich, Milwaukee, Wis.) was reacted with MMA dimer (2.00 g, DuPont Marshall Laboratories, Philadelphia, Pa.) at 65° C. for 8 hours. The sample was then submitted for MALDI mass spectroscopy. Table 5 presents the observed masses (sodiated cations) and relative intensities of a series of products with the number of imines and MMA dimers indicated. The simple adducts are listed first, though they are not the most abundant products. By the time that multiple MMA dimers have reacted with the PEI, one of them will have cyclized with loss of methanol, giving the products in the second section of the table. Cyclization can continue giving the products in the third section of the table. For two of the adducts to have cyclized, there must, of course, be at least two MMA dimers added to the PEI; thus, there are no observed products for two cyclizations with only one MMA dimer added and that section of the Table is indicated as not applicable (NA). The same explanation is appropriate for the section of the table for three cyclizations. In addition to these products, there are also the adducts to the low level of observed cyclic PEI and those products are indicated in the last two sections of the table.

Based upon the structure of the starting polymeric amine, and the mass spectroscopic and nmr results, the resulting linear polymer may be considered to be represented by the schematic structure

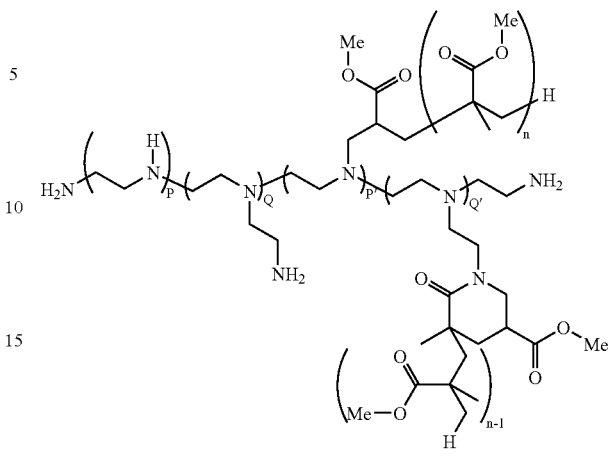

In addition to the two terminal amino groups that could well be reacted, the four repeat units making up the structure are unreacted internal secondary amines, unreacted primary amines on pendant aminoethyl groups, reacted internal amines that can form an adduct, but that cannot cyclize, and reacted aminoethyl groups that may be uncyclized or cyclized (shown cyclized).

TABLE 5

Adducts of MMA dimer to Polyethyleneimine

| | | Number of $MMA_2$ | | | | | | | |
|---|---|---|---|---|---|---|---|---|---|
| | | 1 | | 2 | | 3 | | 4 | |
| | Number of PEI | Mass | Intens. | Mass | Intens. | Mass | Intens. | Mass | Intens. |
| Simple | 3 | | | 569 | 50 | 769 | 15 | | |
| adduct | 4 | 412 | 22 | 612 | 32 | 812 | 10 | | |
| | 5 | 455 | 28 | 655 | 16 | 855 | 6 | | |
| | 6 | 498 | 12 | 698 | 10 | | | | |
| One | 3 | 337 | 12 | 537 | | 737 | 24 | 937 | 11 |
| cycle | 4 | 380 | 96 | 580 | | 780 | 20 | 980 | 7 |
| | 5 | 423 | 100 | 623 | 22 | 823 | 13 | 1023 | |
| | 6 | 466 | 62 | 666 | 11 | 866 | 7 | 1066 | |
| | 7 | 509 | 24 | 709 | 6 | 909 | 6 | | |
| | 8 | 552 | 15 | | | | | | |
| Two | 3 | NA | | | | 705 | 12 | | |
| cycles | 4 | NA | | 548 | 12 | 748 | 14 | 948 | 7 |
| | 5 | NA | | 591 | 42 | 791 | 18 | 991 | 7 |
| | 6 | NA | | 634 | 18 | 834 | 10 | 1034 | 5 |
| | 7 | NA | | 677 | 10 | 877 | 7 | 1077 | 4 |
| | 8 | NA | | | | 920 | 7 | | |
| Three | 4 | NA | | NA | | | | 916 | 7 |
| cycles | 5 | NA | | NA | | 759 | 8 | 959 | 9 |
| | 6 | NA | | NA | | 802 | 7 | 1002 | 8 |
| | 7 | NA | | NA | | 845 | 4 | 1045 | 6 |
| Cyclic PEI | 4 | | | 595 | 14 | | | | |
| simple | 5 | | | 638 | 11 | 838 | 5 | 1038 | 5 |
| adduct | 6 | | | 681 | 7 | 881 | 4 | 1081 | 4 |
| Cyclic PEI | 5 | 406 | 10 | 606 | 8 | 806 | 7 | 1006 | 4 |
| one | 6 | 449 | 11 | 649 | 8 | 849 | 6 | 1049 | 3 |
| cycle | 7 | 492 | 10 | 692 | 6 | 892 | 5 | | |

Of the observed products in Table 5, representative structures include a PEI pentamer with a single simple adduct

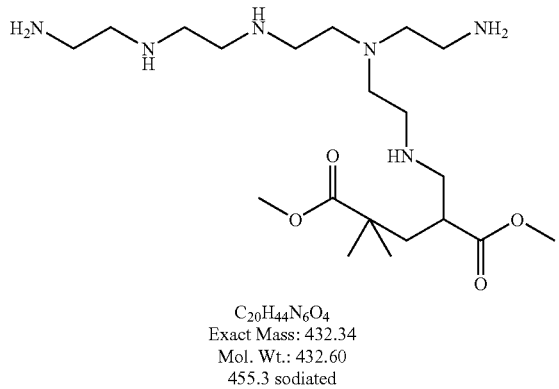

C$_{20}$H$_{44}$N$_6$O$_4$
Exact Mass: 432.34
Mol. Wt.: 432.60
455.3 sodiated and a PEI dimer with two added MMA oligomers

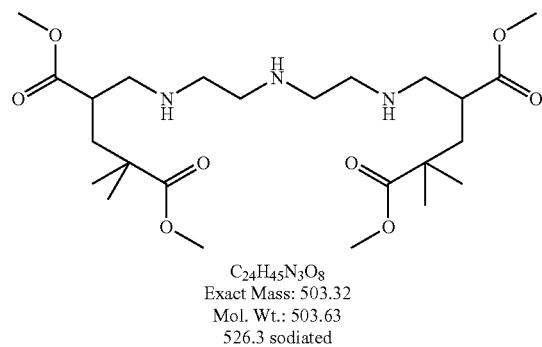

C$_{24}$H$_{45}$N$_3$O$_8$
Exact Mass: 503.32
Mol. Wt.: 503.63
526.3 sodiated

In the next section of Table 5 where one of the adducts is cyclized, the most abundant product had mass 423 and a representative structure is

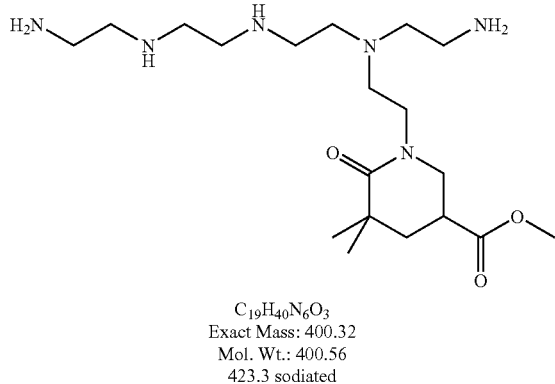

C$_{19}$H$_{40}$N$_6$O$_3$
Exact Mass: 400.32
Mol. Wt.: 400.56
423.3 sodiated

Of the higher mass products, one of the most abundant, based upon mass spectroscopy is given by

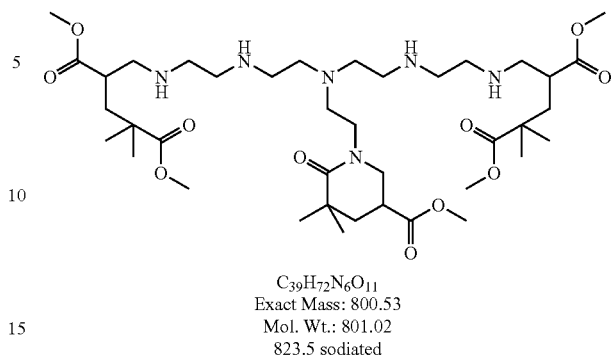

C$_{39}$H$_{72}$N$_6$O$_{11}$
Exact Mass: 800.53
Mol. Wt.: 801.02
823.5 sodiated where three MMA dimers have added to a branched PEI pentamer and one of the adducts has cyclized.

Finally, there are products in the mixture based upon cyclized PEI. A representative sample based upon PEI tetramer with two added MMA dimers is given by the structure

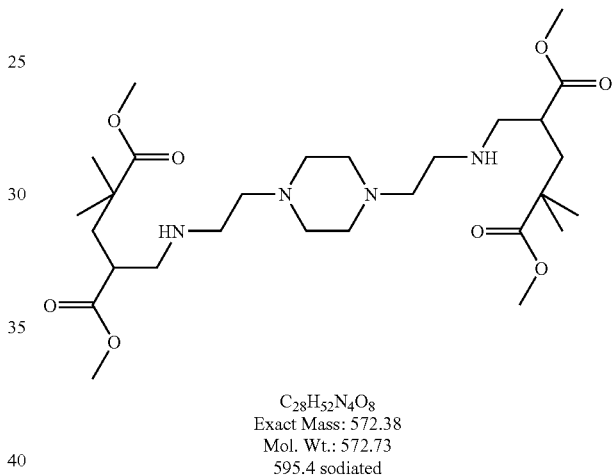

C$_{28}$H$_{52}$N$_4$O$_8$
Exact Mass: 572.38
Mol. Wt.: 572.73
595.4 sodiated

Example 15

Reaction with Polyethyleneimine

Polyethyleneimine (Aldrich, Milwaukee, Wis., catalog number 408719) is a branched polyethyleneimine with P+Q of about 14. The sample (4.23 g, Aldrich, Milwaukee, Wis.) was reacted with methyl methacrylate dimer (2.00 g, DuPont Marshall Laboratories, Philadelphia, Pa.) as in example 13. The sample was then submitted for MALDI mass spectroscopy. The data is presented in Table 6. While generally of higher mass than in example 10, the observed products were similar.

TABLE 6

Products from the addition of MMA dimer to Polyethyleneimine

| | | Number of MMA$_2$ | | | | | | | |
|---|---|---|---|---|---|---|---|---|---|
| | | 1 | | 2 | | 3 | | 4 | |
| | Number of PEI | Mass | Intens. | Mass | Intens. | Mass | Intens. | Mass | Intens. |
| Simple | 2 | 326 | 40 | 526 | 64 | 726 | 7 | | |
| adduct | 3 | 369 | 26 | 569 | 60 | 769 | 10 | | |

TABLE 6-continued

Products from the addition of MMA dimer to Polyethyleneimine

| | | Number of MMA₂ | | | | | | | |
|---|---|---|---|---|---|---|---|---|---|
| | | 1 | | 2 | | 3 | | 4 | |
| | Number of PEI | Mass | Intens. | Mass | Intens. | Mass | Intens. | Mass | Intens. |
| | 4 | 412 | 20 | 612 | 55 | 812 | 14 | | |
| | 5 | 455 | 16 | 655 | 42 | 855 | 10 | | |
| | 6 | 498 | 18 | 698 | 26 | 898 | 10 | | |
| | 7 | 541 | 10 | 741 | 18 | 941 | 8 | | |
| | 8 | | | 784 | 12 | | | | |
| One | 3 | 337 | 20 | 537 | 26 | 737 | 42 | | |
| cycle | 4 | 380 | 100 | 580 | 24 | 780 | 60 | 980 | 6 |
| | 5 | 423 | 82 | 623 | 25 | 823 | 65 | 1023 | 9 |
| | 6 | 466 | 56 | 666 | 22 | 866 | 55 | 1066 | 9 |
| | 7 | 509 | 46 | 709 | 20 | 909 | 38 | 1109 | 9 |
| | 8 | 552 | 30 | 752 | 18 | 852 | 26 | 1152 | 7 |
| | 9 | 595 | 20 | 795 | 10 | 995 | 18 | 1195 | 6 |
| Two | 3 | NA | | 505 | 10 | 705 | 4 | | |
| cycles | 4 | NA | | 548 | 22 | 748 | 6 | 948 | 6 |
| | 5 | NA | | 591 | 28 | 791 | 10 | 991 | 16 |
| | 6 | NA | | 634 | 27 | 834 | 15 | 1034 | 24 |
| | 7 | NA | | 677 | 26 | 877 | 16 | 1077 | 25 |
| | 8 | NA | | 720 | 20 | 920 | 15 | 1120 | 22 |
| | 9 | NA | | 763 | 15 | 963 | 14 | 1163 | 18 |
| | 10 | NA | | 806 | 12 | 1006 | 12 | 1206 | 15 |
| | 11 | NA | | | | 1049 | 8 | 1292 | 10 |
| Three | 5 | NA | | NA | | 759 | 14 | 959 | |
| cycles | 6 | NA | | NA | | 802 | 18 | 1002 | 5 |
| | 7 | NA | | NA | | 845 | 20 | 1045 | 6 |
| | 8 | NA | | NA | | 888 | 13 | 1088 | 8 |
| | 9 | NA | | NA | | 931 | 12 | 1131 | 9 |
| | 10 | NA | | NA | | 974 | 9 | 1174 | 9 |
| | 11 | NA | | NA | | 1017 | 8 | 1217 | 8 |
| Cyclic PEI | 4 | | | 595 | 20 | 795 | 7 | 995 | 16 |
| simple | 5 | | | 638 | 16 | 838 | 6 | 1038 | 11 |
| adduct | 6 | | | 681 | 13 | 881 | 4 | 1081 | 7 |
| Cyclic PEI | 6 | | | 606 | 6 | 806 | 10 | 1006 | 12 |
| one | 7 | | | 649 | 5 | 849 | 6 | 1049 | 9 |
| cycle | 8 | | | 692 | 4 | 892 | 6 | 1092 | 7 |

Example 16

Reaction of Hexyl Amine with Isobutyl Methacrylate Oligomers

This Example demonstrates amination of a oligomer of another methacrylate

To a 20 mL vial equipped with stir bar was added isobutyl methacrylate oligomers (5.00 g, DuPont Marshall Laboratories, Philadelphia Pa.) and hexylamine (2.53 g, Aldrich, Milwaukee, Wis.). This was allowed to stir at 65° C. for 6 hours and then submitted for MALDI mass spectroscopy. The spectra are described in Table 7. In addition to the starting isobutyl acrylate oligomers which showed up as the ions with sodium, there were abundant peaks from the simple amine adduct.

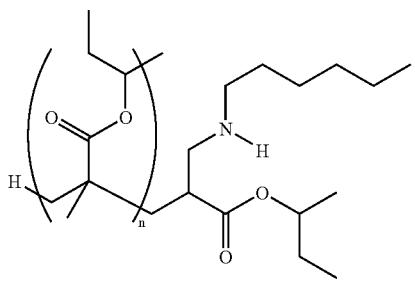

TABLE 7

Mass spectrum of the hexylamine adducts of isobutyl methacrylate oligomers

| Number of iBuMA | Mass of PiBuMA + Na+ | Relative Intensity | Mass + HexNH₃+ | Relative Intensity |
|---|---|---|---|---|
| 0 | 23 | | 102 | |
| 1 | 165 | | 244 | |
| 2 | 307 | | 386 | |
| 3 | 449 | | 528 | 100 |
| 4 | 591 | 62 | 670 | 62 |
| 5 | 733 | 23 | 812 | 32 |
| 6 | 875 | 13 | 954 | 16 |
| 7 | 1017 | 9 | 1096 | 11 |
| 8 | 1159 | 7 | 1238 | 9 |
| 9 | 1301 | 6 | 1380 | 6 |
| 10 | 1443 | 4 | 1522 | 5 |
| 11 | 1585 | 3 | 1664 | 4 |

Example 17

Sequential Reaction of tris(aminoethyl)amine with Isobutyl Methacrylate Oligomers and MMA Dimer This Example demonstrates addition of different oligomers to a polyamine Isobutyl methacrylate oligomers (2.00 g, DuPont Marshall Laboratories, Philadelphia, Pa.) were weighed into a 20 mL vial. TREN [tris(aminoethylamine)] (0.50 g, Aldrich, Milwaukee, Wis.) was weighed out and added to the vial.

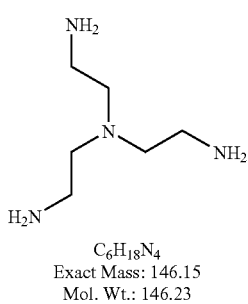

C₆H₁₈N₄
Exact Mass: 146.15
Mol. Wt.: 146.23

A slight yellow tint developed and the system seemed slightly turbid. The mixture was heated at 60° C. for 24 hours and then allowed to cool. The potential products were the addition of one, two and three oligomers to the TREN core. Each of the oligomers had the option of simple addition or ring closing. The sample was analyzed by MALDI mass spectroscopy and the results are given in Table 8. For reference, the observed mass peaks of the sodiated starting material and their intensities are shown in the first line of data. The second set of peaks are the protonated simple adducts and the third line are the observed mono-cyclized products. If further cyclization products were present, they were of low intensity.

TABLE 8

MALDI mass spectroscopy of the products of addition of isobutylmethacrylate oligomers to TREN

| | No. of BMA | | | | | | | | |
|---|---|---|---|---|---|---|---|---|---|
| | 3 | 4 | 5 | 6 | 7 | 8 | 9 | 10 | 11 |
| Sodiated starting oligomer | 449 | 591 | 733 | 875 | 1017 | 1159 | 1301 | 1443 | 1585 |
| Intensity | 100 | 98 | 42 | 29 | 27 | 23 | 20 | 16 | 14 |
| Protonated amine adduct | 573 | 715 | 857 | 999 | 1141 | 1283 | 1425 | 1567 | 1709 |
| Intensity | 74 | 100 | 57 | 35 | 16 | 10 | | | |
| Protonated cyclized adduct | 499 | 641 | 783 | 925 | 1067 | 1209 | 1351 | 1493 | 1635 |
| Intensity | 22 | 92 | 26 | 15 | 8 | | | | |

While it is clear that addition to the TREN molecules occurred, it was not possible to conclusively demonstrate that there were multiple additions to a single TREN, because the addition of two low oligomers would give the same mass result as the addition of one high mass oligomer. Nonetheless, the addition of multiple oligomers to a single TREN was demonstrated by continuing the experiment.

A large excess of MMA dimer (5 mL) was added to the above reaction mixture. The sample was then reheated for 24 hours at 80° C. It was once again submitted for MALDI mass spectroscopy. The mass spectroscopy presented in Table 9 substantiates the course of the second reaction.

TABLE 9

MALDI mass spectroscopy of the addition of iBMA$_n$ and MMA$_2$ to TREN.

| | No. of BMA | | | | | | | | | |
|---|---|---|---|---|---|---|---|---|---|---|
| | 3 | 4 | 5 | 6 | 7 | 8 | 9 | 10 | 11 | 12 |
| BMA$_n$ cyclized adduct | 499 | 641 | 783 | 925 | 1067 | 1209 | 1351 | 1493 | 1635 | 1777 |
| Intensity | | 12 | 14 | 20 | 9 | 10 | 5 | 3 | 2 | |
| BMA$_n$ dicyclized adduct | 425 | 567 | 709 | 851 | 993 | 1135 | 1277 | 1419 | 1561 | 1703 |
| Intensity | | 52 | 67 | 18 | 66 | 20 | 6 | 3 | 2 | 2 |
| BMA$_n$ + 1MMA$_2$ dicyclized | 667 | 809 | 951 | 1093 | 1235 | 1377 | 1519 | 1661 | 1803 | 1945 |
| Intensity | 56 | 10 | 15 | 24 | 6 | 3 | 2 | 2 | 2 | |
| BMA$_n$ + 2MMA$_2$ tricyclized | 835 | 977 | 1119 | 1261 | 1403 | 1545 | 1687 | 1829 | 1971 | 2113 |
| Intensity | | | | | | 2 | 2 | 1 | | |

The peaks shown are for the protonated species. Almost all of the product was cyclized as a result of the additional heating. After cyclization, it is clear that there were an appreciable number of double additions of iBMA$_n$ to the TREN because there were an appreciable number of double cyclizations with loss of isobutanol. There were also products with one MMA dimer that had also undergone cyclization with loss of methanol. The most abundant of these, having a mass of 667 is given by the structure

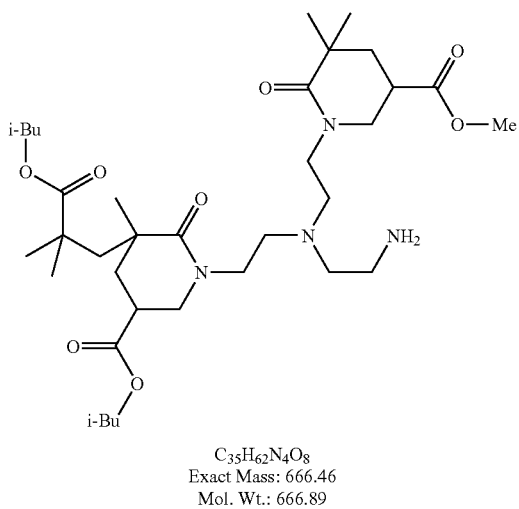

C$_{35}$H$_{62}$N$_4$O$_8$
Exact Mass: 666.46
Mol. Wt.: 666.89

Finally, there are a few peaks that suggest the addition and cyclization of one iBMA$_n$ and two MMA dimers, though these peaks are too weak to be reliably assigned. It has been demonstrated that adducts of two or more different oligomers may be added to a polyamine.

What is claimed is:

1. A compound having the structure

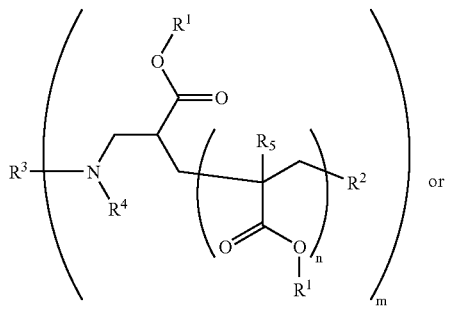

-continued

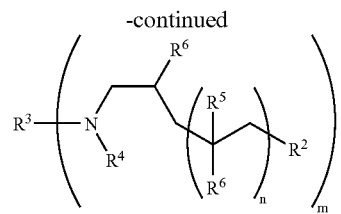

wherein R$^1$ and R$^2$ are independently H, alkyl of 1-20 carbon atoms, aryl, substituted alkyl of 1-20 carbon atoms, or substituted aryl; R$^3$ is H, alkyl of 1-100 carbon atoms, or substituted alkyl or a polymer; R$^5$ is methyl, hydrogen or hydroxymethyl; n=1-100; and m+m'=1-100 and is equal to or less than the number of reactive amino groups on R$^3$.

2. A compound of claim 1 wherein R$^3$ is derived from a polymeric amine.

3. The compound of claim 2 wherein m is 2 and n is between 3 and 50.

4. The compound of claim 2 wherein m and n are each independently between 3 and 50.

5. A compound of claim 1 wherein R$^3$ is derived from a polymeric and polyfunctional amine.

6. A compound of claim 1 wherein R$^3$ is derived from a bifunctional amine.

7. A compound of claim 1 wherein n is from 1 to 10.

8. A compound of claim 1 wherein m is from 2 to 50.

9. A compound of claim 1 wherein R$^3$ is derived from an amine-terminated polymer.

10. A compound of claim 1 wherein R$^3$ is derived from a diamino-terminated polymer or a polymeric polyamine.

11. A compound of claim 1 wherein R$^5$ is methyl.

12. A compound of claim 1 wherein R$^2$ is derived from a macromonomer of an alkyl methacrylate.

13. A product comprising a compound having a structure as described in claim 1, said product selected from the group consisting of inks, dispersions, adhesives, resists, and automotive and architectural coatings, paints, or finishes, including high solids, aqueous, or solvent-based finishes.

14. A product comprising a compound having a structure as described in claim 1, said product selected from the group consisting of dispersants, compatibilizers, adhesives, adhesion promoters, biological agents, compatibilizers, coupling agents, crosslinkers, curing agents, de-foamers, emulsifiers, flocculent, grafting agents, photopolymerizable materials, resists, stabilizers, surface active agents, surfactants, and viscosity modifiers.

* * * * *